United States Patent [19]

Hodson et al.

[11] Patent Number: 5,347,998
[45] Date of Patent: Sep. 20, 1994

[54] BREATH ACTUATED INHALER HAVING AN ELECTROMECHANICAL PRIMING MECHANISM

[75] Inventors: Peter D. Hodson, Trowell; Eric A. Baum; David K. Smith, both of Loughborough, all of Great Britain; Anton Kuepper, Kaarst, Fed. Rep. of Germany; Matthew J. Wilby, Loughborough, Great Britain

[73] Assignee: Minnesota Mining and Manufacturing Company, St. Paul, Minn.

[21] Appl. No.: 965,406
[22] PCT Filed: Jul. 8, 1991
[86] PCT No.: PCT/GB91/01116
   § 371 Date: Dec. 23, 1992
   § 102(e) Date: Dec. 23, 1992
[87] PCT Pub. No.: WO92/00770
   PCT Pub. Date: Jan. 23, 1992

[30] Foreign Application Priority Data

Jul. 9, 1990 [GB] United Kingdom ............ 9015077.2

[51] Int. Cl.5 .............................................. A61M 11/00
[52] U.S. Cl. ........................ 128/200.23; 128/203.12; 222/162; 222/504
[58] Field of Search ............... 128/200.23, 200.14, 128/200.21, 200.22, 200.18, 203.12, 203.15, 204.21, 204.23; 222/153, 162, 504

[56] References Cited

U.S. PATENT DOCUMENTS

| | | | |
|---|---|---|---|
| 3,187,748 | 6/1965 | Mitchell et al. | 128/200.23 |
| 3,388,834 | 6/1968 | Hart | 222/504 |
| 3,456,644 | 7/1969 | Thiel | 128/200.23 |
| 3,456,645 | 7/1969 | Brock | 128/200.23 |
| 3,456,646 | 7/1969 | Phillips et al. | 128/200.23 |
| 3,565,070 | 2/1971 | Hanson et al. | 128/200.23 |
| 3,598,294 | 8/1971 | Hedrick et al. | 128/200.23 |
| 3,605,738 | 9/1971 | Ciranna | 128/200.23 |
| 3,636,949 | 1/1972 | Kropp | 128/200.23 |
| 3,732,864 | 5/1973 | Thompson et al. | 128/200.23 |
| 3,789,843 | 2/1974 | Armstrong et al. | 128/200.23 |
| 3,814,297 | 6/1974 | Warren | 222/402.13 |
| 3,826,413 | 7/1974 | Warren | 128/200.23 X |
| 3,858,581 | 1/1975 | Kamen | 604/155 |
| 4,648,393 | 3/1987 | Landis et al. | 128/200.23 |
| 4,678,106 | 7/1987 | Newell | 128/200.23 X |
| 5,069,204 | 12/1991 | Smith et al. | 128/200.23 |
| 5,193,745 | 3/1993 | Holm | 128/200.23 X |

FOREIGN PATENT DOCUMENTS

| | | |
|---|---|---|
| 147028 | 7/1985 | European Pat. Off. |
| 186280 | 7/1986 | European Pat. Off. |
| 3040641 | 5/1982 | Fed. Rep. of Germany |
| 1269554 | 4/1972 | United Kingdom |
| 1335378 | 10/1973 | United Kingdom |
| 1392192 | 4/1975 | United Kingdom |
| 2061116 | 5/1981 | United Kingdom |
| 87/04354 | 7/1987 | World Int. Prop. O. |

*Primary Examiner*—Edgar S. Burr
*Assistant Examiner*—Eric P. Raciti
*Attorney, Agent, or Firm*—Gary L. Griswold; Walter N. Kirn; Douglas E. Reedich

[57] ABSTRACT

An inhalation device for use with a pressurized aerosol canister. The device involves an electromechanical mechanism for applying a priming force to the aerosol canister prior to or at the start of inhalation. The device also involves a blocking mechanism. The electromechanical mechanism electromechanically applies to the aerosol canister a priming force sufficient to actuate the aerosol canister, and the blocking mechanism prevents the priming force from actuating the aerosol canister until inhalation is detected.

13 Claims, 7 Drawing Sheets

BREATH ACTUATED INHALER HAVING AN ELECTROMECHANICAL PRIMING MECHANISM

BACKGROUND OF THE INVENTION

1. Field of the Invention

This invention relates to inhalation activatable dispensers for use with aerosol containers which contain medicaments for inhalation therapy, are pressurized with liquid propellants, and include a metering valve through which a series of metered medicament doses can be dispensed. In particular the invention relates to inhalation activatable dispensers which do not require the patient to prime the dispenser by manually applying a load to the valve prior to or during use.

2. Description of the Related Art

Inhalation activatable dispensers for use with aerosol container assemblies of the type described above are known, their general purpose being to afford proper coordination of the dispensing of a dose of medicament with the inhalation of the patient thereby allowing the maximum proportion of the dose of medicament to be drawn into the patient's bronchial passages. Examples of such dispensers are described in British Patent Specification Nos. 1,269,554, 1,335,378, 1,392,192 and 2,061,116 and U.S. Pat. Nos. 3,456,644, 3,456,645, 3,456,646, 3,565,070, 3,598,294, 3,814,297, 3,605,738, 3,732,864, 3,636,949, 3,789,843 and 3,187,748 and German Patent No. 3,040,641.

European Patent No. 147028 discloses an inhalation activatable dispenser for use with an aerosol container in which a latch mechanism releasing vane is pivotally mounted in an air passage between an aerosol outlet valve and a mouthpiece, which latch mechanism cannot be released if force to activate the dispenser is not applied before a patient inhales.

The dispenser generally comprises a housing having a mouthpiece and an air passage therethrough terminating at the mouthpiece, the housing being adapted to receive an aerosol container and having a support block with a socket adapted to receive the stem of the valve of the aerosol container and a through orifice communicating between the socket and the air passage, and latch means having parts movable between an engaged position in which movement of the container and the support block toward each other upon the application of a force to bias the container and the support block toward each other is prevented and a release position in which movement of the container and the support block toward each other in response to said force is permitted causing the stem to move to its inner discharge position, the latch means comprising a vane mounted on the housing in the air passageway between the orifice and the mouthpiece for movement toward the mouthpiece under the influence of inhalation through the mouthpiece to release the latch means in which the vane moves toward the mouthpiece from a blocking to a nonblocking position with respect to the passageway in response to inhaling at the mouthpiece and releases the latch means only during the application of said force to bias the container and support block toward each other.

This inhalation device has been received favorably by patients and doctors since it not only overcomes the hand-lung coordination problem but it does so at a very low triggering flow rate (approximately 30 liters/minute) essentially silently, and with a very compact design barely larger than a standard inhaler. It is necessary to manually prime the inhalation device with a lever to apply the bias to the container prior to use.

U.S. Pat. No. 4,648,393 discloses an electrically-operated metered dose inhaler in which a mechanical valve blocking means is withdrawn by the action of a solenoid moving in response to the closing of a switch; the switch constitutes an electromechanical breath actuation means which responds to inhalation by the patient. The disclosed device relies entirely upon mechanical priming of the device by application of force to a spring.

WO87/04354 discloses a medical dosing device for the discharge of medicament for inhalation which comprises a handheld holder for a medicine container from which medicine is discharged via a valve into an air channel for inhalation by means of initiation of an activation device. The valve is operationally connected with a control unit arranged on initiation of the activation device to control the discharge valve for intermittent opening and closing repeatedly within an inhalation period. The control unit is an electronically controlled unit which activates an electrically controlled discharge valve.

SUMMARY OF THE INVENTION

It is an object of the present invention to provide an inhalation device for use with a pressurised aerosol container equipped with a metered dose dispensing valve which does not require manual priming for firing the valve.

Therefore according to the present invention there is provided an inhalation device for use with a pressurized aerosol canister equipped with a metered dose dispensing valve movable between a closed position and a dispensing position, the device comprising a housing for supporting said canister in communication with a patient port for administration of a composition dispensed from the dispensing valve, the device comprising electromechanical means for applying a priming force, prior to or at the start of inhalation through the patient port, to said canister or dispensing valve sufficient for actuation of the dispensing valve and blocking means to prevent said priming force actuating the dispensing valve until patient inspiration through the patient port is detected.

DETAILED DESCRIPTION OF THE INVENTION

The invention provides a means of electromechanically priming, i.e., applying the force required to actuate the valve, and optionally resetting, a mechanical metered dose inhaler having a blocking action which prevents actuation prior to inhalation, by use of an electrical motor or solenoid. The blocking action may be removed upon detection of inhalation by electromechanical or purely mechanical means. The motor or solenoid is used to provide a bias between the valve stem and container, e.g., by compressing or extending biasing means such as a spring or other resilient means, e.g., coil or leaf spring, hydraulic or pneumatic system. The force exerted by this stored energy is then applied to any part of the aerosol can or valve, either prior to inhalation, or at the start of inhalation, depending upon construction of the breath actuation means. This priming action may typically be initiated by the patient pressing a button or opening a mouthpiece cover which operates an electric switch. The motor or solenoid then applies a load to the resilient means, driving directly or indirectly via a lever, rack and pinion, worm gear or cam. When the patient inhales and triggers the release of the blocking mechanism, the preloaded resilient means moves the aerosol can relative to the valve stem and fires the metered dose valve.

Immediately, or shortly, after the valve is fired, the same or a different motor or solenoid may be used to reset the valve to its rest position by moving the aerosol canister or the valve stem back to their relative rest positions. Alternatively, the valve may be reset by the action of its own internal spring once the motor or solenoid has been driven in reverse to remove the load.

The same, or a different motor or solenoid may also be used as a means of releasing the blocking action of a blocking mechanism to fire the valve.

The invention provides a means of priming a breath actuated metered dose inhaler, in which the breath actuation means has a blocking action, without the need for the patient to manually apply a load to prime the device thereby overcoming the potential problem of children, the elderly and the infirm not being able to apply enough force or possessing sufficient manual dexterity to prime such a device, and presenting the possibility of making the inhaler fully automatic.

The use of resilient priming means in a blocking type breath actuated inhaler allows the load to be applied slowly over an extended period prior to inhalation, thus greatly reducing the power requirements of the motor or solenoid compared to that needed for direct actuation of the valve at the time of inhalation. Subsequent breath actuated removal of the blocking means can readily be sufficiently rapid to ensure delivery of a dose of medicament near the start of inhalation.

Initiation of the priming action by the opening of the mouthpiece would both ensure the provision of ample time for priming of the device and remove the need for the patient to take any additional action.

The electromechanical priming means may be advantageously used in association with electromechanical resetting of the valve. Thus, the valve is no longer reliant upon its own internal spring for resetting, permitting a reduction in the force of this spring. This will in turn, reduce the amount of work needed to fire the valve, again allowing the use of a smaller motor or solenoid, with an attendant reduction in battery power requirement.

Use of an electromechanical valve resetting means in this way, if operated automatically immediately or very shortly after firing of the valve, would have the important advantage of avoiding the possibility of vapor lock formation in the metering tank, which may occur if the valve is left in the fired position for a significant period, or is allowed to reset when the canister is not upright. The device may incorporate means to allow resetting of the valve only when the canister is upright and/or indicating means to warn the patient to hold the canister upright in order to prevent the possibility of vapor lock formation in the metering tank.

The presence of electronic means within the device readily allows the possibility of other electronic control or monitoring means being incorporated, e.g., control means to limit the dosage frequency available to the patient, means for counting doses dispensed or available and to prevent actuation of the device if the label claim number of doses in the aerosol canister has been dispensed in order to prevent vapor lock or "tail-off" problems leading to reduced doses of medicament.

BRIEF DESCRIPTION OF THE DRAWING

The invention will now be described with reference to the accompanying drawings in which.

DESCRIPTION OF THE PREFERRED EMBODIMENTS

FIGS. 1 to 5 show an inhalation device comprising a housing (2) having a patient port (4) in the form of a mouthpiece, the housing containing an aerosol canister (6) equipped with a metering valve (8). The stem of the valve is positioned within a nozzle block (10) which is configured to direct medicament emitted from the valve towards the mouthpiece. Actuation of the valve is achieved by movement of the aerosol canister (6) relative to the valve stem. This movement is blocked prior to inhalation through the mouthpiece by the patient, by a breath actuated blocking mechanism (12). The blocking mechanism is shown in the form of a pivoted vane which is illustrated in its blocking position with its end (14) preventing depression of the canister to a sufficient extent to allow valve actuation. On inhalation the vane pivots to the top of the mouthpiece allowing movement of the canister for valve actuation. Other blocking mechanisms which may be released on inspiration may be employed.

Figure 1:
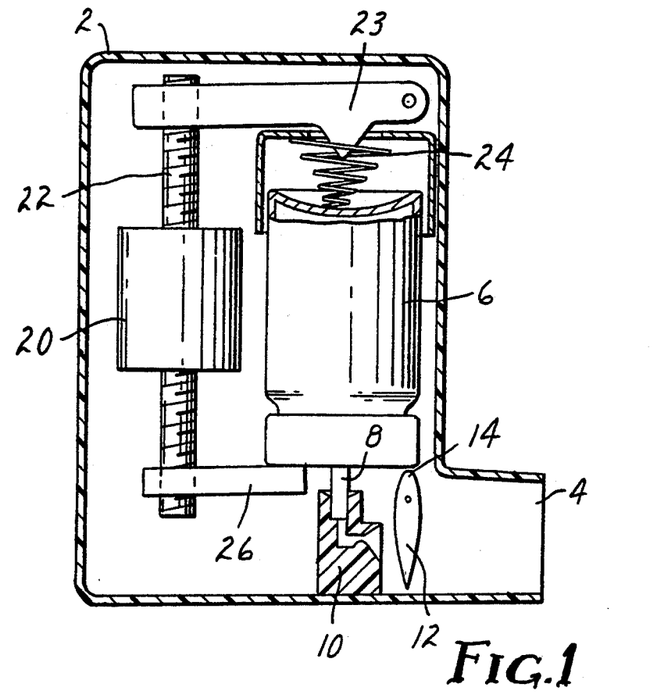
FIGS. 1 to 5 represent diagrammatic sections through inhalation devices in accordance with the invention.

Referring to FIG. 1, the device may be provided with a switch, e.g., in the form of a button (not shown) or a mouthpiece cover (not shown) which on actuation energizes motor (20) which drives threaded lead screw (22) causing movement of load applicator (23) to a stop position, compressing priming spring (24) and moving valve reset arm (26) clear of the valve. When the patient inhales, the blocking action of mechanism (12) is removed and spring (24) pushes the canister down to fire the valve. After a short time delay, or alternatively, when the patient presses the button or closes the mouthpiece cover, the motor is reenergized so as to drive the load applicator back up to the stop position, at the same time returning the canister to the rest position and resetting the valve.

Figure 2:
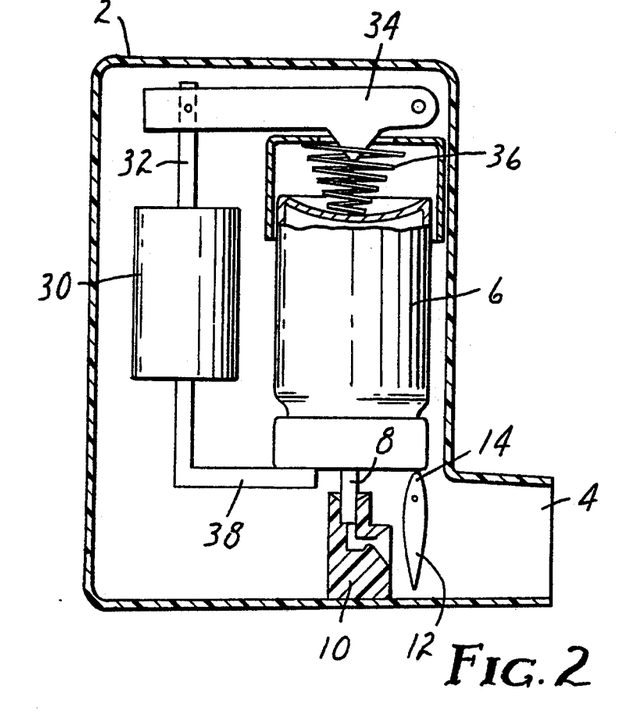

Referring to FIG. 2, the solenoid (30) is energized by a switch as in FIG. 1 which causes movement of plunger (32) and associated load applicator (34) causing priming spring (36) to be compressed and valve reset arm (38) to be moved clear of the valve. When the patient inhales, the blocking action of breath actuation mechanism (12) is removed and the spring pushes down on the canister to fire the valve.

After a short time delay, or alternatively when the patient presses the button or replaces the mouthpiece cover, the solenoid is deenergized so as to allow the priming spring (36) and/or the integral spring of the solenoid to drive the plunger back to the stop position, at the same time returning the canister to the rest position and resetting the valve.

Figure 3:
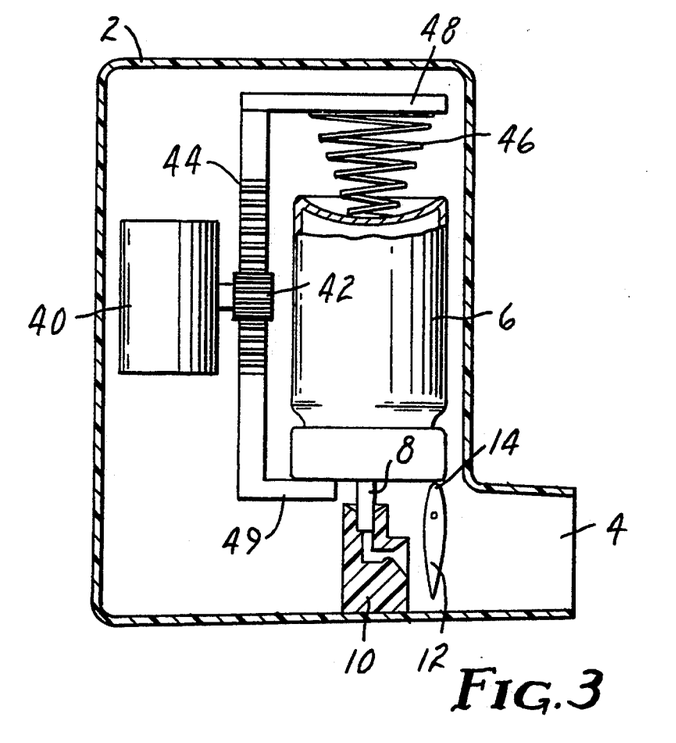

Referring to FIG. 3, the patient presses the button or opens the mouthpiece cover to energize motor (40) as in FIG. 1, such that rotation of pinion (42) causes rack (44)

to be driven down to the stop position, thereby compressing priming spring (46) by load applicator (48) and moving valve reset arm (49) clear of valve (8). When the patient inhales, the blocking action of breath actuation mechanism (12) is removed and the spring pushes the canister down to fire the valve.

After a short time delay, or alternatively when the patient presses the button or replaces the mouthpiece cover, motor (40) is reenergized and drives rack (44) back up to the stop position, at the same time returning canister (6) to the reset position and resetting the valve.

Figure 4:
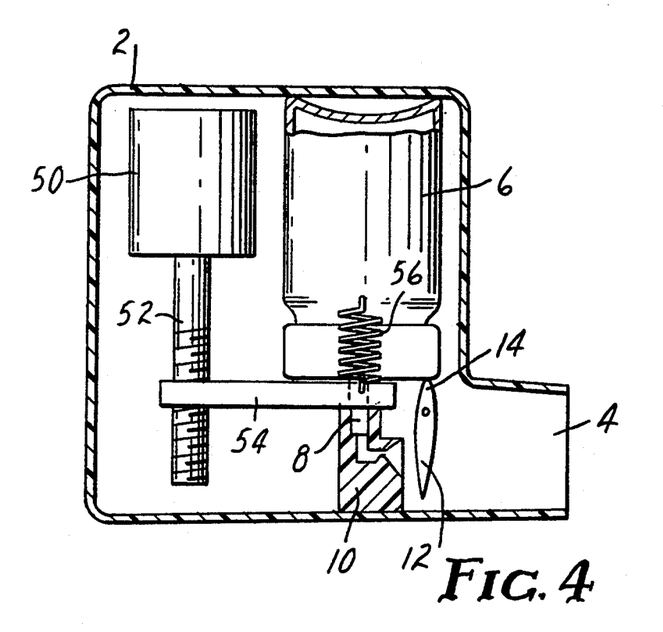

Referring to FIG. 4, the patient presses the button or opens the mouthpiece cover as in FIG. 1 to energize motor (50), such that threaded lead screw (52) is driven to the stop position, thereby moving the valve reset arm (54) down clear of the valve and tensioning priming spring (56).

When the patient inhales, the blocking action of mechanism (12) is removed and spring (56) pulls down canister (6) to fire the valve.

After a short time delay, or alternatively when the patient presses the button or replaces the mouthpiece cover, motor (50) is reenergized and rotates threaded lead screw (52) which moves valve reset arm (54) back up to the stop position, at the same time returning canister (6) to the rest position and resetting valve (8).

Figure 5:
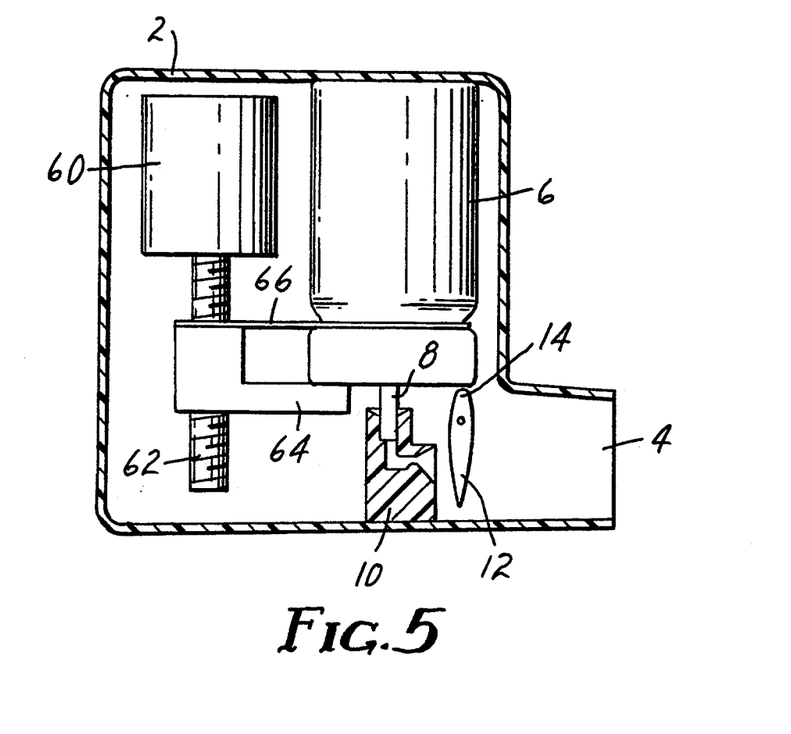

Referring to FIG. 5, the patient presses the button or opens the mouthpiece cover as in FIG. 1 to energize motor (60), such that threaded lead screw (62) is driven to the stop position, thereby moving valve reset arm (64) down clear of the valve (8) and bending the priming spring (66).

When the patient inhales, the blocking action of the mechanism (12) is removed and spring (66) pulls down canister (6) to fire valve (8).

After a short time delay, or alternatively when the patient presses the button or replaces the mouthpiece cover, motor (60) is reenergized and drives valve reset arm (64) back up to the stop position, at the same time returning canister (6) to the rest position and resetting valve (8).

Figure 6:
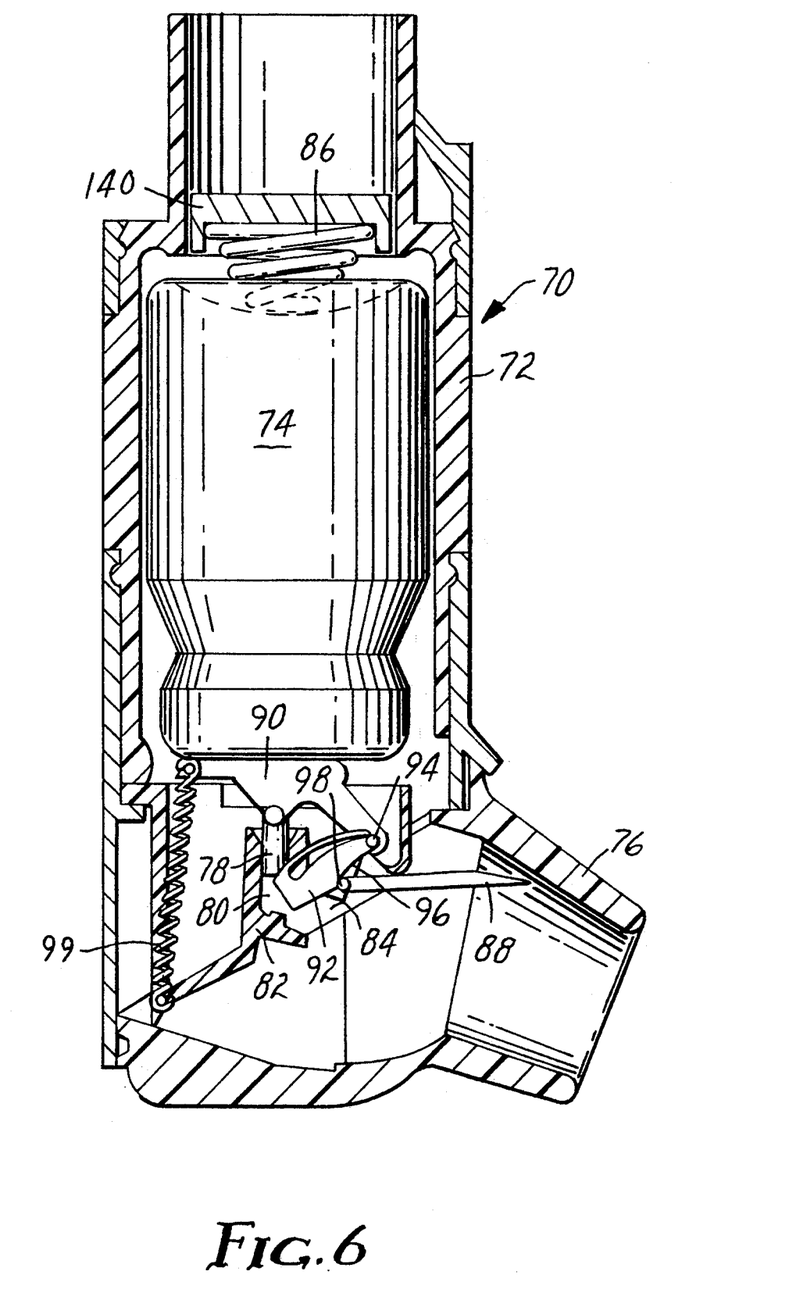
FIGS. 6 to 9 represent diagrammatic sections through a further inhalation device of the invention.

FIG. 6 illustrates a breath actuated pressurized aerosol dispenser of the type disclosed in European Patent No. 147028, but modified for use with the present invention. The lever assembly used to compress the cocking spring has been removed to allow the device to be primed by electromechanical means described hereinafter. The unmodified device is commercially available under the trade name AUTOHALER from Minnesota Mining and Manufacturing Company.

The dispenser (70) comprises a housing (72) containing an aerosol container (74) and incorporating a mouthpiece (76) which may optionally be provided with a removable cover (not shown). The aerosol container (74) is equipped with a metering valve (not shown) possessing a hollow stem (78) which is located within a socket (80) in the nozzle block (82). The nozzle block (82) is also provided with a passage way (84) which communicates with the socket (80) and mouthpiece (76) to allow for the release of a dose of medicament. Discharge of the metering valve is effected by relative movement between the body of the aerosol canister (74) and the valve stem (78) under the influence of cocking spring (86). This movement is, when the device is not in use, blocked by a breath actuated blocking mechanism.

The breath actuated blocking mechanism comprises a vane (88) which is pivotally mounted within the mouthpiece (76) and a rocker element (90) which supports a catch (92) pivotally mounted thereon at (94). When the blocking mechanism is in its blocking position (see FIG. 8), then movement of the aerosol canister (74) is prevented by the rocker element (90). Movement of the rocker element (90) is in turn prevented by the catch (92) which has a curved surface (96) engaging the curved surface (98) of the vane (88). Thus, it is not possible to dispense the contents of the aerosol canister (74) before the patient has inhaled through the mouthpiece (76).

When a patient inhales through the mouthpiece (76), the developing air flow causes pivotal movement of the vane (88) as shown. The curved surface (98) of the vane (88) and the curved surface (96) of the catch (92) effectively act as cooperating roller surfaces such that pivotal movement of the vane (88) causes the curved surface (98) thereof to rotate in one direction and the curved surface (96) of the catch (92) to rotate in the opposite direction. In this manner, the catch (92) is displaced from a blocking to a nonblocking position which permits pivotal movement of the rocker element (90) and, in turn, movement of the aerosol canister (74) relative to the valve stem (78), thereby firing the valve and releasing a metered dose of medicament. The rocker element (90) is biased by a spring (99) to its blocking position when patient inspiration is halted.

A method of priming such a breath actuated pressurized dispenser using electromechanical means will now be described with reference to the inhalation device shown in FIG. 7.

Figure 7:
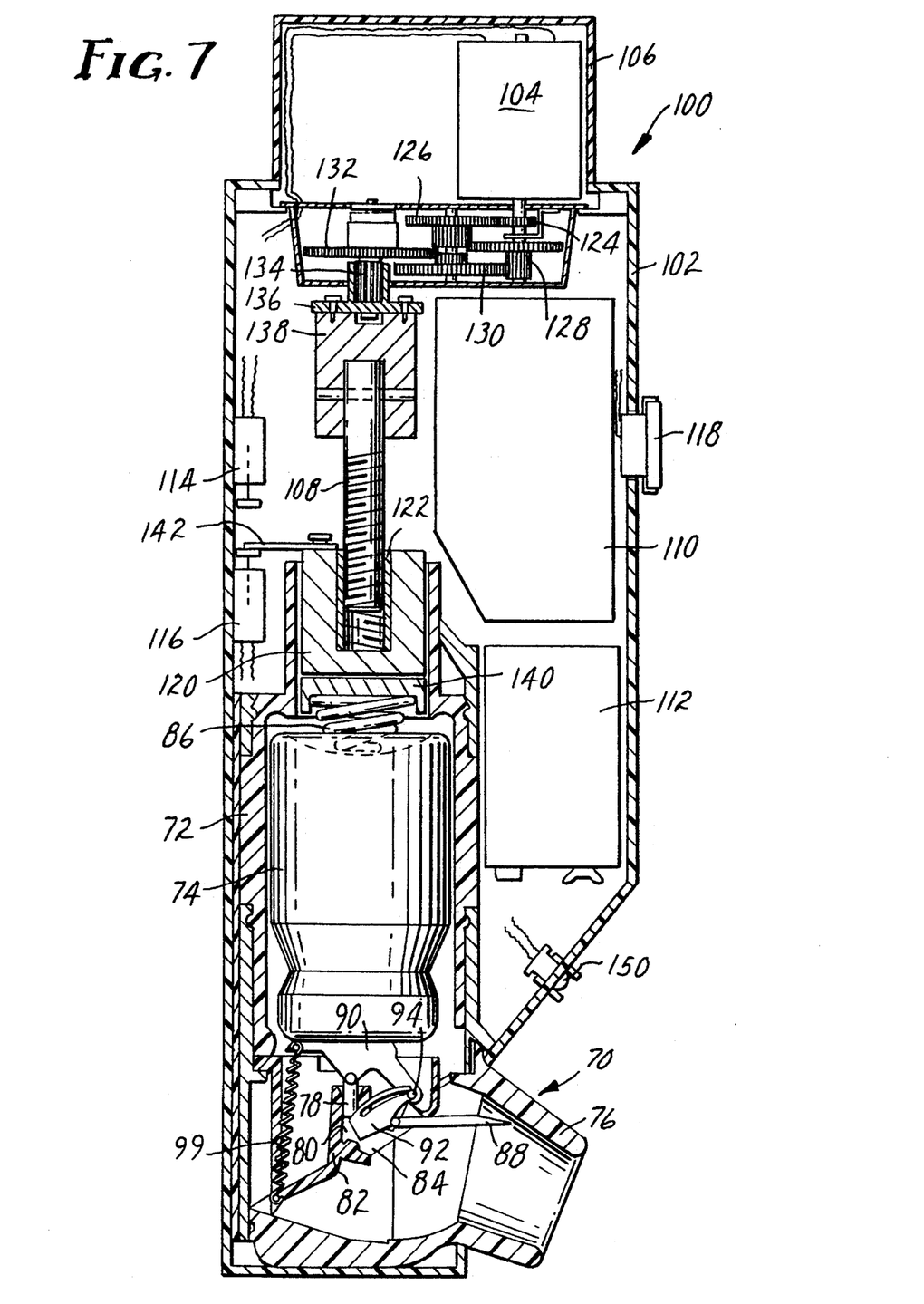

Referring to FIG. 7, the inhalation device (100) comprises an outer casing (102) which encloses the dispenser (70) shown in FIG. 6 and the components of the electromechanical priming means. The main components of the device are: a d.c. servo motor (104) contained in a housing (106), a lead screw (108), an electronic circuit board (110), a battery (112), two limit switches (114 and 116), a push button switch (118) and a carriage (120). For reasons of clarity the electrical connections between certain components have deliberately been omitted.

The carriage (120) is free to travel up and down the lead screw (108) but is prevented from rotating by contact with the housing (72) of the dispenser (70). The friction between the carriage (120) and the walls of the housing (72) is desirably low.

The carriage (120) has an insert (122), typically made of phosphor bronze, with a threaded internal surface which matches the thread on the lead screw (108).

When the device (100) is not in use, the carriage (120) is positioned at the top of its travel thereby, allowing the cocking spring (86) to relax and the aerosol canister (74) to move upwards under the influence of the internal valve spring (not shown).

To operate the device (100), the patient depresses the push button (118) sending a signal to the electronics (110). The electronics (110) then energize the d.c. motor (104) via a cross over relay arrangement (not shown), with the correct polarity for driving the carriage (120) down the lead screw (108).

This is achieved as follows. The drive pinion (124) of the servo motor drives a first gear (126) which contacts a second gear (128) which rotates freely around its axle and contacts a third gear (130). The third gear (130) which also rotates freely around its axle is in contact with a fourth gear (132) whose other end constitutes the final drive in the form of splined shaft (134).

A horn (136) is attached to the splined shaft (134) and a housing block (138) is fixed to the horn (136). The lead screw (108) is located in a circular sectional recess hole in the housing block (138), e.g., by means of a suitable adhesive and locking pin (shown in hidden relief). Thus, the lead screw (108) can be made to rotate in unison with the servo motor (104) at a rate determined by the values of the reduction gearing (126 to 132) and the motor voltage and losses, and in a direction determined by the polarity of the motor.

When the lead screw (108) is rotated by the servo motor (104) as previously described, the carriage (120) with its threaded insert (122) moves downwards compressing the cocking spring (86) between the spring guide (140) and the aerosol canister (74). This downwards motion of the aerosol canister (74) continues until an arm (142) attached to the carriage (120) contacts a lower limit switch (116) sending a signal to the electronics (110) which cuts the power to the servo motor (104). The time taken to prime the device (100) thus depends on the stroke of the carriage (120), the rate of revolution of the lead screw (108) and the pitch of the thread on the lead screw (108).

The inhalation device (100) is stable in the primed state as the spring (86) will remain compressed by the carriage (120) with the servo motor (104) deenergized, because it cannot rotate the lead screw (108) in reverse against the mechanical advantage of the lead screw (108) and reduction gearing (126 to 132). The dispenser (70) and servo motor assembly (106) are constrained physically from moving apart because both are firmly attached to the outer casing (102), the former by adhesive and the latter by lugs (144).

Figure 8:
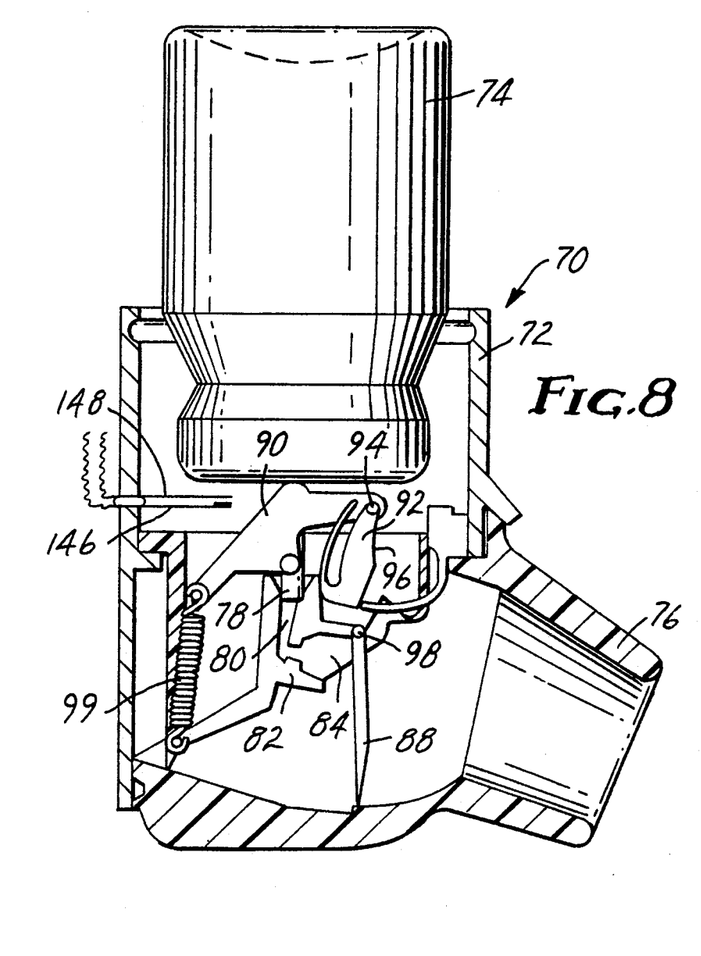

FIG. 8 shows the dispenser (70) in this stable primed state where it awaits patient inspiration at the mouthpiece (76) to displace (lift) the vane (88) and fire the device. The vane (88) of the breath actuation mechanism is in its blocking position and the catch (92) and rocker element (90) are rotated such that the heel of the rocker element (90) is uppermost. In the primed state, the priming mechanism is typically under a compressive load of around 30N. Therefore, to prevent the device being left in this stressed state for long periods of time, it is preferably fitted with a 'time-out' facility, whereby, if the device has not fired as a result of patient inspiration within a predetermined time after priming has taken place (e.g., 30 seconds), the electronics (110) will reset the device as if it had fired.

Figure 9:
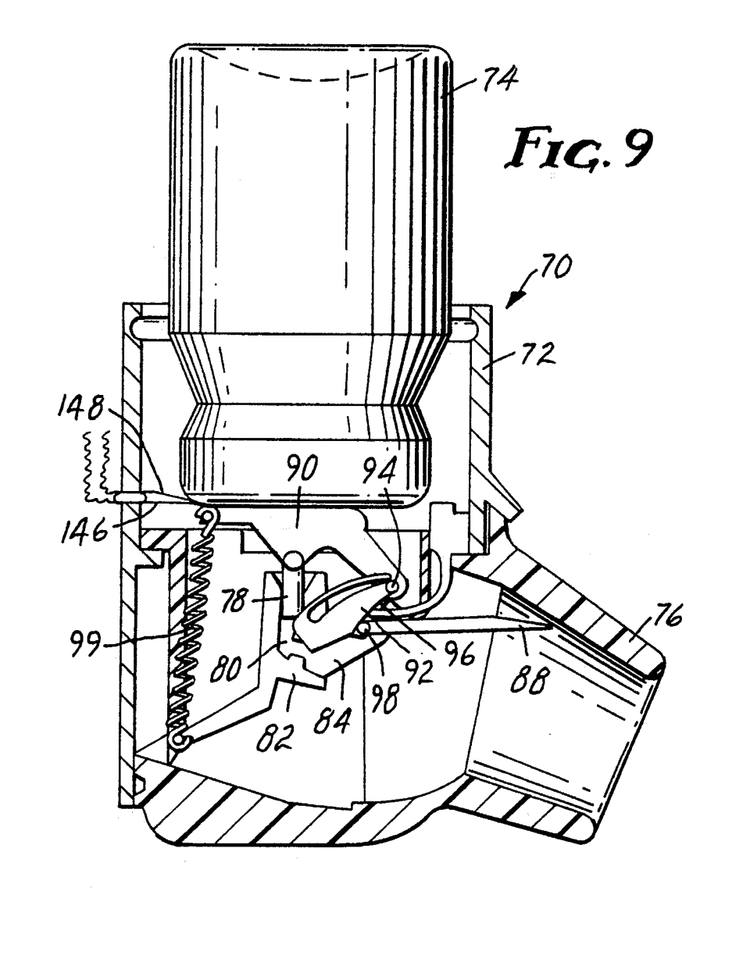

FIG. 9 shows the dispenser (70) in its fired state after the patient has breath actuated the device. As a result of the vane (88) lifting, the catch (92) and rocker element (90) rotate to allow the aerosol canister (74) to move downwards under the influence of the cocking spring (not shown), thereby firing the valve and releasing a dose of medicament. In the course of this action two electrical contacts (146 and 148), one or both of which are compliant, e.g., of brass foil, are brought together to complete an electrical circuit. This sends a signal to the electronics (110) which then initiates the reset procedure.

The servo motor (104) is energized with the opposite polarity to reverse the rotation of the lead screw (108), thereby causing the carriage (120) to move upwards until the arm (142) contacts the upper limit switch (114). This sends a signal to the electronics (110) to deenergize the servo motor (104). The device is now reset.

The time between the detection of the valve firing by the closing of contacts (146 and 148) and the initiation of the reset procedure can be dictated by the electronics. Indeed it is advantageous to introduce a short delay so that the important breath holding period after inhalation of the dose is not interrupted by the sensation of the device resetting. However, the delay should not be so long as to risk the problems of "vapor lock" in the valve of the aerosol canister.

An indicator lamp (150) is lit when the device is in the primed state, as shown in FIG. 8, which is extinguished when the device is fired by patient inspiration or is reset following a 'time-out' condition, thereby warning the patient that the device is no longer primed.

Figure 10:
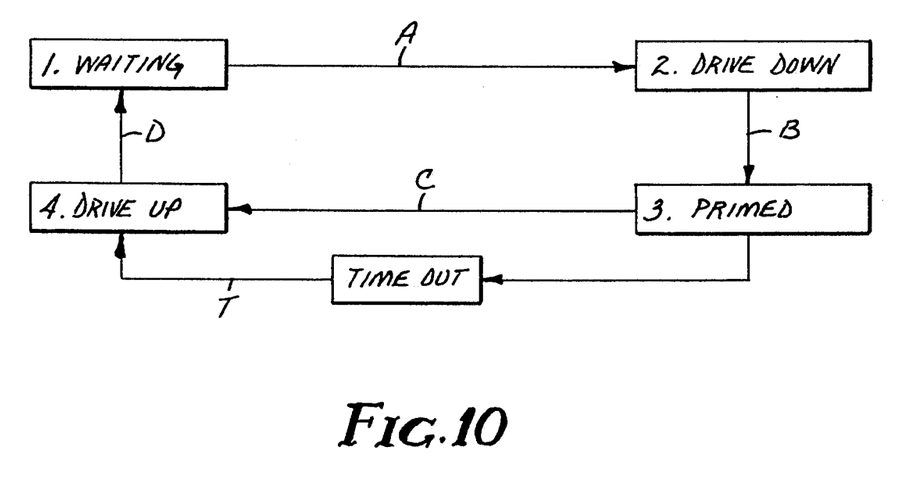
FIG. 10 is a state diagram of the logic of the inhalation device of FIGS. 6 to 9.

The logic of the above device (100) is represented schematically in the form of a state diagram by FIG. 10. Referring to FIG. 10, the device is normally in state 1 where it is essentially dormant and using negligible power. When signal A is received as a result of the "on" button (118) being pressed the device goes into state 2, whereby the motor (104) is energized to compress the spring (86). This process continues until signal B is received from the lower limit switch (116) to indicate that the full stroke has been completed, at which point the device is primed (state 3). The indicator lamp (150) is then illuminated and the timer started.

The device stays in this state until signal C is received by the closing of contacts (146 and 148) to indicate that the device has been fired or signal T is received from the timer to indicate that a 'time-out' has occurred. In either case, the indicator lamp (150) is extinguished and optionally a second timer started to delay the reset. Alternatively, the reset may be commenced immediately (state 4). The servo motor (104) then turns in reverse and as the downwards force of the carriage (120) is removed the aerosol canister (74) is reset under the action of the valve spring. The carriage (120) continues upwards until signal D is received from the upper limit switch (114) at which time the device is back in state 1 waiting for signal A.

Figure 11:
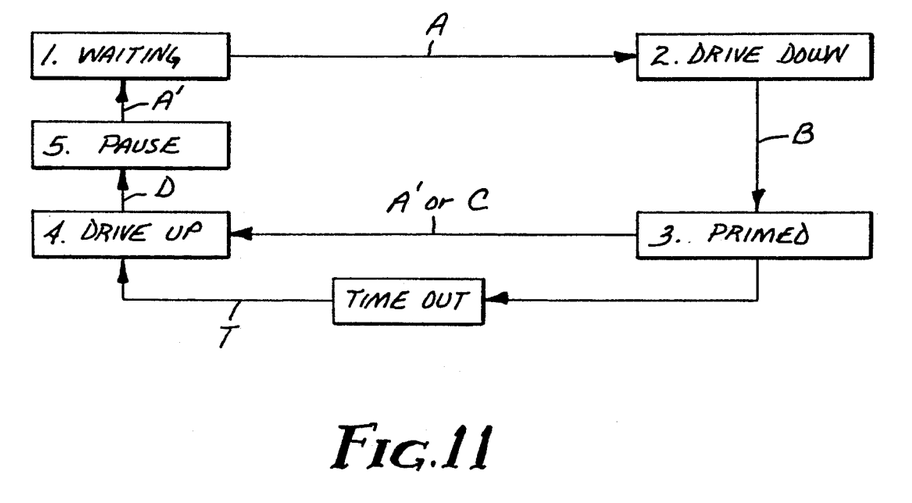
FIG. 11 is a state diagram of the logic of an alternative inhalation device of the invention.

FIG. 11 represents an alternative schematic for a device having a mouthpiece cover which is hinged to operate an on-off switch replacing the momentary acting push-button (118).

The dormant state 1 is the same, as are the driving down and primed states 2 and 3. However, the device will go from state 3 to state 4 if it receives either the C or T signals that would indicate normal delivery or 'time-out', or a A' signal indicating that the mouthpiece cover has been closed.

Once in state 4 the reset is performed as before (with or without the optional delay period previously mentioned) and the cocking spring decompressed until signal D is received from the upper limit switch (114).

If the electronics went from state 3 to state 4 because it received signal A', then the pause state 5 will be skipped and the device will go straight to state 1. However, if the transition from state 3 to state 4 was due to signal C or T, then the mouthpiece cover is still open and the electronics will pause in state 5 until the cover is closed (generating a A' signal).

In either case once the device is in the rest state (state 1) it will stay there until the cover is opened again, which could be straight away (for a second dose) or more likely after an undefined period of time has elapsed.

"AUTOHALER" (Minnesota Mining and Manufacturing Company) is a registered trade mark.

We claim:

1. An inhalation device comprising: a pressurized aerosol canister comprising a metered dose dispensing vale movable between a closed position and a dispensing position; a housing for supporting said canister in communication with a patient port; electromechanical means for generating and storing a priming force, prior to or at the start of inhalation through the patient port, and applying said priming force to said canister, said priming force being sufficient for actuation of the dispensing valve; and blocking means to prevent said priming force from actuating the dispensing valve prior to patient inspiration through the patient port, wherein said electromechanical means further comprises an electric motor or solenoid, a drive arrangement, a load applicator, and a resilient biasing means, wherein the drive arrangement communicates between the electric motor or solenoid and the load applicator, and wherein the resilient biasing means is positioned between the load applicator and the canister.

2. A device as claimed in claim 1 comprising an electric motor and in which the drive arrangement comprises a threaded lead screw.

3. A device as claimed in claim 1 comprising an electric motor and in which the drive arrangement comprises a rack and pinion.

4. A device as claimed in claim 1 in which the biasing means comprises a spring.

5. A device as claimed in claim 1 additionally comprising a valve reset means for resetting the valve after firing.

6. A device as claimed in claim 5 comprising control means to actuate the valve reset means immediately after firing the valve.

7. A device as claimed in claim 5 in which the valve reset means comprises means for automatically resetting the valve after a fixed time interval following priming of the device and during which time the device has not been actuated.

8. A device as claimed in claim 5 additionally comprising means to prevent valve reset if the canister is not substantially vertical.

9. A device as claimed in claim 1 additionally comprising means to indicate whether the device is primed.

10. A device as claimed in claim 1 in which the blocking means comprises a pivoted vane.

11. A device as claimed in claim 1 in which the blocking means comprises electromechanical means for removing blocking of the priming force.

12. A device as claimed in claim 1 comprising control means to prevent actuation of the device after a predetermined number of doses has been dispensed.

13. A device as claimed in claim 5 additionally comprising indicating means to warn a patient to hold the canister in a substantially vertical position.

* * * * *